(12) United States Patent
McHugh Karow et al.

(10) Patent No.: US 8,011,499 B2
(45) Date of Patent: Sep. 6, 2011

(54) SUTURE TRAY PACKAGE

(75) Inventors: Meredith McHugh Karow, Hatboro, PA (US); Robert Cerwin, Pipersville, NJ (US); John P. Harrison, Greer, SC (US)

(73) Assignee: Ethicon, Inc., Sommerville, NJ (US)

( * ) Notice: Subject to any disclaimer, the term of this patent is extended or adjusted under 35 U.S.C. 154(b) by 9 days.

(21) Appl. No.: 12/335,645

(22) Filed: Dec. 16, 2008

(65) Prior Publication Data

US 2010/0147708 A1 Jun. 17, 2010

(51) Int. Cl.
*A61B 17/06* (2006.01)
(52) U.S. Cl. ........ 206/63.3; 206/380; 206/227; 206/303
(58) Field of Classification Search ................ 206/63.6, 206/380, 382, 210, 225, 227, 303, 428; 600/585
See application file for complete search history.

(56) References Cited

U.S. PATENT DOCUMENTS

| | | | | |
|---|---|---|---|---|
| 3,280,971 A | * | 10/1966 | Regan, Jr. ..................... | 206/63.3 |
| 3,338,401 A | * | 8/1967 | Regan, Jr. ..................... | 206/63.3 |
| 3,376,973 A | | 4/1968 | Marks et al. | |
| 3,759,376 A | | 9/1973 | Lisowski | |
| 3,857,484 A | | 12/1974 | Thyen | |
| 3,972,418 A | * | 8/1976 | Schuler et al. ............... | 206/63.3 |
| 3,985,227 A | | 10/1976 | Thyen et al. | |
| 4,008,802 A | | 2/1977 | Freitag | |
| 4,034,850 A | | 7/1977 | Mandel et al. | |
| 4,084,692 A | * | 4/1978 | Bilweis ......................... | 206/403 |
| 4,311,050 A | * | 1/1982 | Bessman ........................ | 73/427 |
| 4,424,898 A | | 1/1984 | Thyen et al. | |
| 4,846,343 A | * | 7/1989 | Rupert .......................... | 206/303 |
| 4,903,826 A | * | 2/1990 | Pearce ........................ | 206/63.3 |
| 5,123,528 A | | 6/1992 | Brown et al. | |
| 5,131,533 A | | 7/1992 | Alpern | |
| 5,131,534 A | | 7/1992 | Brown et al. | |
| 5,154,283 A | | 10/1992 | Brown | |
| 5,197,597 A | * | 3/1993 | Leary et al. .................. | 206/63.3 |
| 5,228,565 A | * | 7/1993 | Sinn ............................. | 206/63.3 |
| 5,341,823 A | * | 8/1994 | Manosalva et al. ........... | 128/898 |
| 5,350,060 A | * | 9/1994 | Alpern et al. ................ | 206/63.3 |
| 5,392,903 A | | 2/1995 | Sinn | |
| 5,407,071 A | * | 4/1995 | Lawhon et al. ............... | 206/388 |
| 5,462,162 A | | 10/1995 | Kaplan | |
| 5,472,081 A | | 12/1995 | Kilgrow et al. | |
| 5,491,954 A | | 2/1996 | Sobel | |
| 5,491,955 A | | 2/1996 | Sobel | |
| 5,575,382 A | | 11/1996 | Sobel et al. | |
| 5,628,395 A | | 5/1997 | Daniele et al. | |
| 5,660,024 A | | 8/1997 | Ivanov et al. | |
| 5,664,404 A | | 9/1997 | Ivanov et al. | |
| 5,704,469 A | | 1/1998 | Daniele et al. | |
| 5,769,214 A | | 6/1998 | Zatarga | |

(Continued)

FOREIGN PATENT DOCUMENTS

EP 168172 A1 1/1986

(Continued)

*Primary Examiner* — David T Fidei
(74) *Attorney, Agent, or Firm* — Emil Richard Skula (57) ABSTRACT

A novel suture tray package is disclosed. The package has a floor member and a plurality of curvilinear walls extending up from the top of the floor member and forming suture tracks. The walls extend in a spiral manner from the central section of the floor member to the periphery. Extending radially outwardly about the periphery are platform sections in communication with the tracks and optionally containing needle park members and pledget park members.

17 Claims, 5 Drawing Sheets

U.S. PATENT DOCUMENTS

| | | | |
|---|---|---|---|
| 6,076,659 A | 6/2000 | Baumgartner et al. | |
| 6,241,089 B1 * | 6/2001 | Grobecker | 206/310 |
| 6,398,022 B1 * | 6/2002 | Mou et al. | 206/308.1 |
| 6,464,071 B2 | 10/2002 | Baumgartner | |
| 6,481,568 B1 * | 11/2002 | Cerwin et al. | 206/63.3 |
| 6,520,325 B1 * | 2/2003 | Simpson | 206/303 |
| 6,533,112 B2 | 3/2003 | Warnecke | |
| 2001/0004966 A1 * | 6/2001 | Warnecke | 206/63.3 |
| 2002/0069617 A1 | 6/2002 | Dey et al. | |
| 2004/0050721 A1 | 3/2004 | Roby et al. | |
| 2004/0177594 A1 | 9/2004 | Dey et al. | |
| 2005/0020940 A1 * | 1/2005 | Opie et al. | 600/585 |
| 2007/0227914 A1 * | 10/2007 | Cerwin et al. | 206/63.3 |

FOREIGN PATENT DOCUMENTS

| | | |
|---|---|---|
| EP | 577993 A1 | 1/1994 |
| EP | 749725 A2 | 12/1996 |
| FR | 1537018 A | 8/1968 |
| WO | WO 2004/007300 | 1/2004 |

* cited by examiner

SUTURE TRAY PACKAGE

TECHNICAL FIELDS

The field of art to which this invention relates is packaging, in particular, packaging for surgical sutures.

BACKGROUND OF THE INVENTION

Surgical sutures are well known in the art. Surgical sutures are typically woven from conventional, biocompatible materials. Although sutures may be made from natural materials such as silk and "gut", sutures are primarily made from synthetic polymers such as polyesters, lactides, glycolides, polyolefins, caprolactones, polyolefins, and the like including copolymers. Surgical sutures are typically used with conventional surgical needles pre-attached to one or both ends. A surgical suture having a surgical needle attached to one end is commonly referred to as a single armed suture, while a suture having a surgical needle attached to both ends is commonly referred to as a double armed suture. A surgical needle is typically a curved or partially curved elongated member having a distal piercing point or tip and a proximal mounting end. The distal end may also have cutting edges to assist in penetration through tissue. Surgical needles are typically constructed from biocompatible materials, in particular metals, including stainless steels. The mounting end of a surgical needles may have a drilled bore hole for receiving the suture end, or a channel may be formed in the distal end of the needle for receiving the suture end. In either case, the suture end is mechanically secured in the bore hole or channel in a conventional manner, for example, by mechanically swaging or compressing a section of the proximal end about the suture. It is also known to use sutures without surgical needles attached for certain surgical procedures such as ligating. For certain types of surgical procedures, for example, heart valve fixation, pledget members may be mounted to the surgical sutures to assist in preventing the sutures from cutting through or damaging tissue.

Packages and packaging for surgical sutures and needles are critical in providing an undamaged, sterile needle to the surgeon during a surgical procedure. There are a variety of known suture packages that can be used to package surgical sutures and needles. One type of package is a folder package. Such packages typically have an array of flaps and panels that are folded about a suture or a plurality of sutures in order to secure the suture in the folder. Such folders typically have conventional needle parks mounted to a panel for receiving and retaining surgical needles, for example, a foam strip with slits. Folder packages protect sutures during handling and shipping, and also provide for ease of sterilization by allowing the penetration of sterilant gases to the sutures. Suture tray packages have also been developed. The suture tray packages are typically molded structures having tracks for receiving sutures. A needle park structure may be molded into the tray. The tray packages have a number of advantages over the folder packages. It is known that many sutures can kink or take a set when loaded into a folder package. This is disadvantageous to both the surgeon and the patient. Tray packages tend to eliminate such kinking. Another advantage of tray packages is that they may be used with high speed machinery in automated loading and packaging processes. And yet another advantage is the cost of manufacturing tray packages. A further advantage is ease of dispensing the sutures. During a critical surgical procedure, such as a heart valve replacement or coronary artery bypass graft procedure, a number or sutures are required by the surgeon to successfully complete the procedure. Time is of the essence since it is in the patient's best interest to complete the procedure in the shortest possible amount of time to avoid complications. Tray and folder packages have been developed which may contain a quantity of sutures, which are necessary to complete the procedure. Dispensing is critical to a successful procedure, and tray packages have been developed which provide for quick dispensing without tangling. It is known that tangling can be an issue with folder packages that contain multiple sutures. However, loading multiple sutures into a tray or folder package may result in certain disadvantages.

Although the tray packages known in the art are useful, there is a constant search in this art for new packages having novel and improved qualities, features and properties that protect sutures and facilitate dispensing during a surgical procedure.

SUMMARY OF THE INVENTION

Accordingly, a novel tray package for sutures is disclosed. The tray package has a floor member having a top surface, a bottom surface, an outer periphery, a center and a central area about the center. A plurality of platform sections extend out from the floor member about the periphery of the floor member. And, a plurality of wall members extend up from the top surface of the floor member and extend outward from the central area toward the outer periphery of the floor member in a preferably spiral manner. The wall members are preferably curvilinear. The wall members have opposed outer surfaces, and the wall members are spaced from each other such that a suture track is formed between the outer surfaces of adjacent wall members and the top surface of the floor member. Optionally, needle park members and pledget park members extend from the top surface of the floor member in platform sections.

These and other aspects and advantages of the present invention will become more apparent from the following description and accompanying drawings.

DETAILED DESCRIPTION OF THE INVENTION

The suture tray packages of the present invention can be made of a variety of conventional polymeric materials useful in suture tray packages. The materials include polymeric materials such as polypropylene, high density polyethylene, poly(ethylene terephthalate), and the like. The suture tray packages of the present invention may be manufactured using various conventional manufacturing processes and techniques including injection molding, thermoforming, welding, machining, mechanical assembly, and any combination of these, and the like. It is particularly preferred to use injection molding.

Referring to FIGS. 1-4, a suture tray package 10 of the present invention is illustrated. The package 10 is seen to have substantially planar floor 30, although the floor may be bowed, curved or stepped or combinations thereof. As seen in FIGS. 1-4, floor 30 is substantially circular in shape, but may have other geometric configurations including square, elliptical, oval, etc., and combinations thereof, and the like. Floor 30 is seen to have top 34 and bottom 37. The floor 30 has outer periphery 40, and floor 30 is seen to have a plurality of radially extending platform sections 42 having floor sections 35. The extending platform sections 42 give the periphery 40 an undulating configuration. Although not preferred, the platform sections 42 may be contained within the floor 30 without extensions. The floor 30 has center 60. Extending upwardly from the top 34 of floor 30 about the periphery 40 is the optional peripheral wall 50. Peripheral wall 50 is seen to have outer surface 52, inner surface 54 and top 56. The peripheral wall 50 is seen to generally follow the contour of the periphery 40, including the sections 58 in the undulating platform sections 42. Although not preferred, the packages 10 of the present invention may be made and used without having a peripheral wall 50

Figure 6:
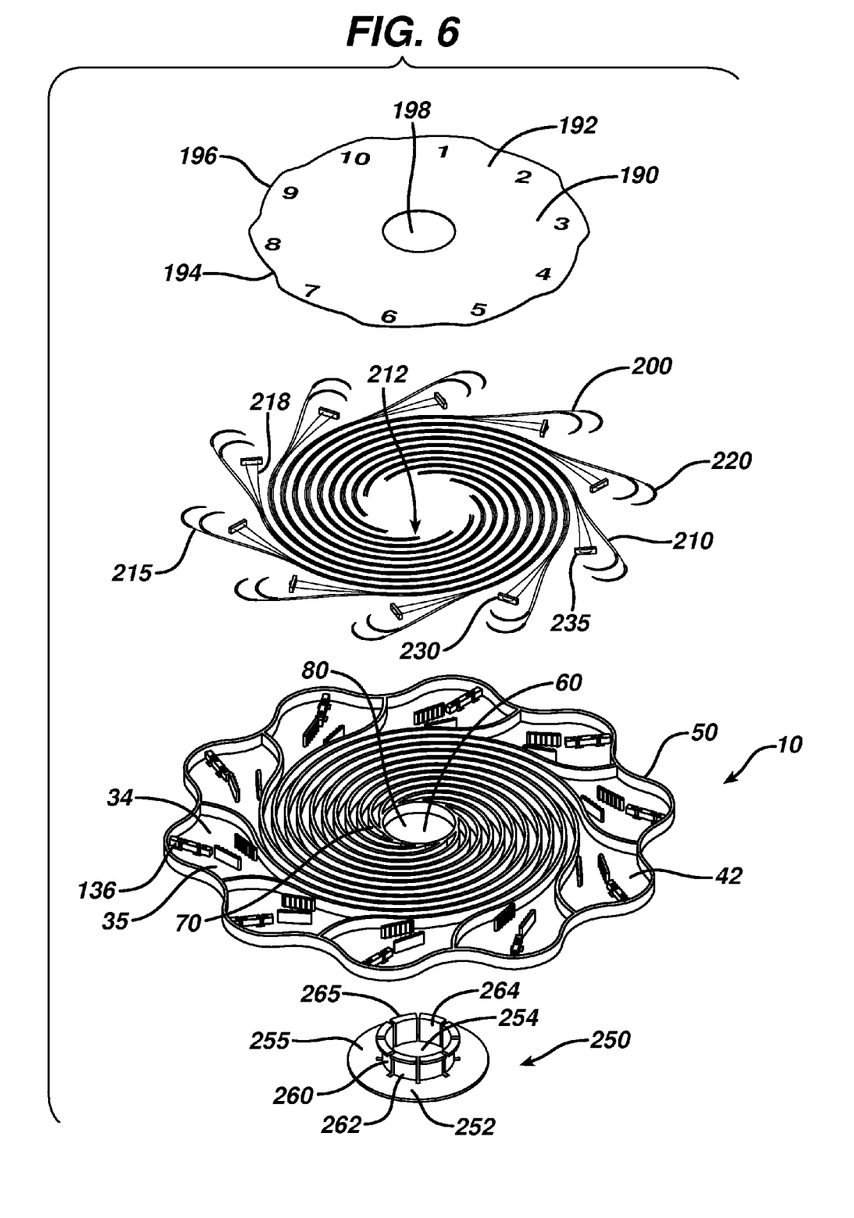
FIG. 6 is an exploded perspective view of a package of the present invention illustrating the package, a cover, double-armed sutures loaded into the tracks of the package, and an optional rotation platform.

Center 60 is seen to have thereabout circular central region 62. Alternatively, central region 62 may have other configurations including square, elliptical, rectangular and the like and combinations thereof. Floor section 38 is optionally contained in central region 62. Surrounding central region 62 is the optional central wall 70. Central wall 70 extends upwardly from the top 34 of floor member 30, and has inner surface 72, outer surface 74 and top 76. Optionally, all or part of the floor section 38 in the central area 62 of the floor 30 within the wall 70 is removed to provide for a finger opening 80. Only the periphery of floor section 38 adjacent to wall 70 is shown in the FIGS. Optionally, a plurality of removable, break-away annular sections (not shown) surround opening 80 to allow for adjustability of opening 80 for different size fingers. When grasping a novel package 10 of the present invention, the health care professional would insert a finger into finger opening 80, facilitating dispensing of sutures and manipulation of the package 10, and providing for rotation of package 10 about the finger. Opening 80 may also be utilized as an opening for a spindle or other mechanical device to facilitate automated suture loading into package 10 on a loading or winding machine. Referring to FIG. 6, an optional spindle structure 250 is seen to have a flat annular base plate member 252 with opening 254 therethrough, and top 255. A plurality of cantilevered members 260 having living hinged ends 262 and free ends 264 extends up from the top 255 of base plate member 252 about the periphery of opening 254. The members 260 are seen to have flange members 265 extending radially outward from the ends 264. The optional spindle 250 is mounted to package 10 by inserting the members 260 into opening 80 through the bottom 37 of floor 30 package 10 by deflecting the members 260 radially inward, and pushing the members through until the flange members 265 extend over the tops 76 and 94 of walls 70 and 90, respectively. The package 10 is then able to rotate about spindle structure 250.

Extending outward from the outer surface 74 of wall 70 in a substantially spiral manner are the suture track walls 90. Walls 90 also are seen to extend upwardly from the top 34 of floor member 30. Walls 90 are seen to have opposed surfaces 92 and tops 94. The walls 90 are seen to have a curvilinear configuration, although the tracks could have other configurations such as radial, straight or angulated spokes, combinations of straight and curved sections, pluralities of straight, angulated sections, and the like. A track 110 is seen to be formed between each pair of walls 90. The suture track 110 is seen to have bottom 112, and opposed sides 115 formed by surfaces 92 of walls 90. The suture tracks 110 have inner ends 114 adjacent to wall 70 and outer ends 116 adjacent to platform sections 42. Ends 116 are in communication with platform sections 42. Each wall 90 is seen to have an inner end 95 connected to the outer surface 74 of the wall 70. The walls 90 also have an outer end 97 that optionally connects to the inner surface 54 of peripheral wall 50. It should be noted that the ends 95 and 97 may be free or unattached. Each track 110 is seen to have a vacuum opening 118 in communication with a passage or opening 39 extending through floor 30. The openings 118 and 39 are preferably located near or inner ends 114 of track 110, but may be located anywhere along track 110. If desired, each track 110 may have multiple openings 118 and 39. Although it is preferred to have walls 50 and 70, those skilled in the art will appreciate that the tray package 10 of the present invention may be utilized without one or both of these walls. The packages 10 as illustrated are seen to have a single track 100 for each platform section 42. Although not illustrated, an alternate embodiment of the packages 10 of the present invention will have two or more tracks for each platform section 42, or a track 110 may be in communication with two or more tracks.

Part of each platform section 42 of periphery 40 is a park platform section 100. Each park platform section 100 is in communication with a track 110. As illustrated in FIGS. 1-6, the park platform sections 100 are bounded by the surfaces 92 of opposed track walls 90 and the inner surface 54 of section 58 of outer wall 50. The park platform sections 100 are also seen to be located in floor sections 35 of floor 30. Park platform sections 100 can also contain optional structures such as conventional needle parks for receiving, holding and retaining surgical needles. As seen in FIGS. 1-6, the package 10 of the present invention contains optional needle park 120. The needle park 120 is seen to have three members 130, 140, and 150, respectively. Member 130 extends up from top 34 of section 35. Member 130 has cantilevered arm 132 having radially inwardly extending section 134, downwardly extending arm 136 having end 138. End 138 can move in opening 112 in floor section 35 when deflected. Adjacent to member 130 is member 140, which also extends up from top 34 of flow section 35. Member 140 is similarly seen to have inwardly extending section 144, downwardly extending arm 146 having end 148. End 148 can similarly move in opening 112 in floor section 35 when deflected. On the radially outward side 141, the engagement edge 143 is seen to extend radially outward along the outward side 141. Member 150 extends up from surface 34 of floor section 35 in alignment with member 140. Member 150 has on the radially outward side 151, the engagement edge 153, which extends radially outward along the outward side 151. The needle park 120 as illustrated is capable of receiving two surgical needles in openings 124 and 126, however it will be appreciated by those skilled in the art that similar needle parks may be utilized that are designed and constructed to hold one surgical needles or multiple surgical needles (i.e., in excess of two). Other types of conventional needle parks may also be used in the packages 10 of the present invention, including foam or plastic members with slits, grooves, or clips. It is also possible to utilize the tray packages 10 of the present invention without needles parks, e.g., with ligatures or unarmed sutures. The needle park 120 is particularly useful for double-armed sutures, i.e., sutures having surgical needles mounted to both ends.

Figure 1:
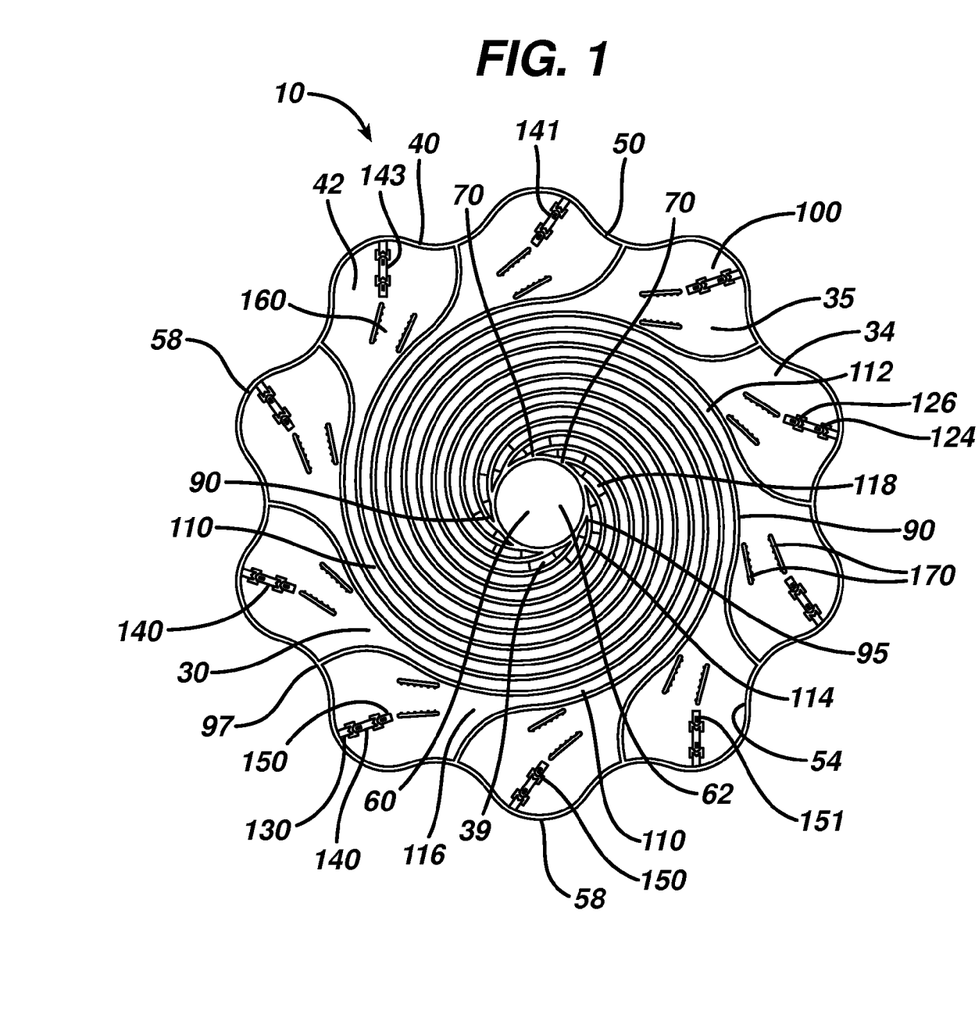
FIG. 1 is plan view of a suture tray package of the present invention.
Figure 2:
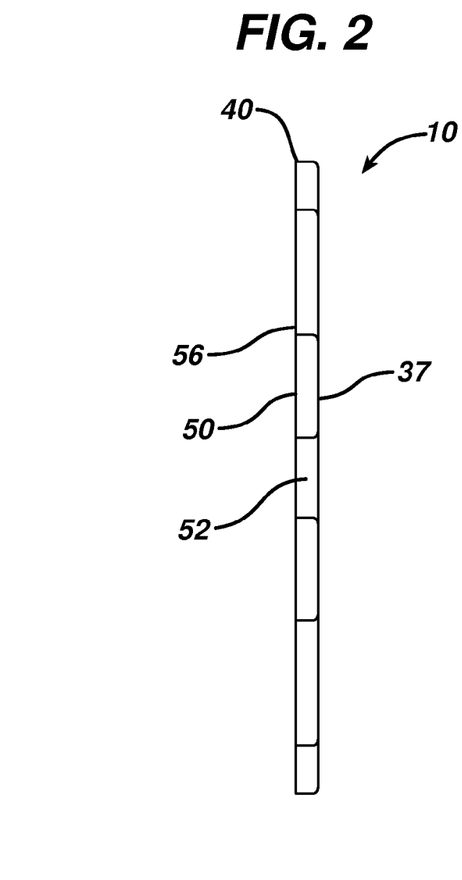
FIG. 2 is a side view of the package of FIG. 2.
Figure 3:
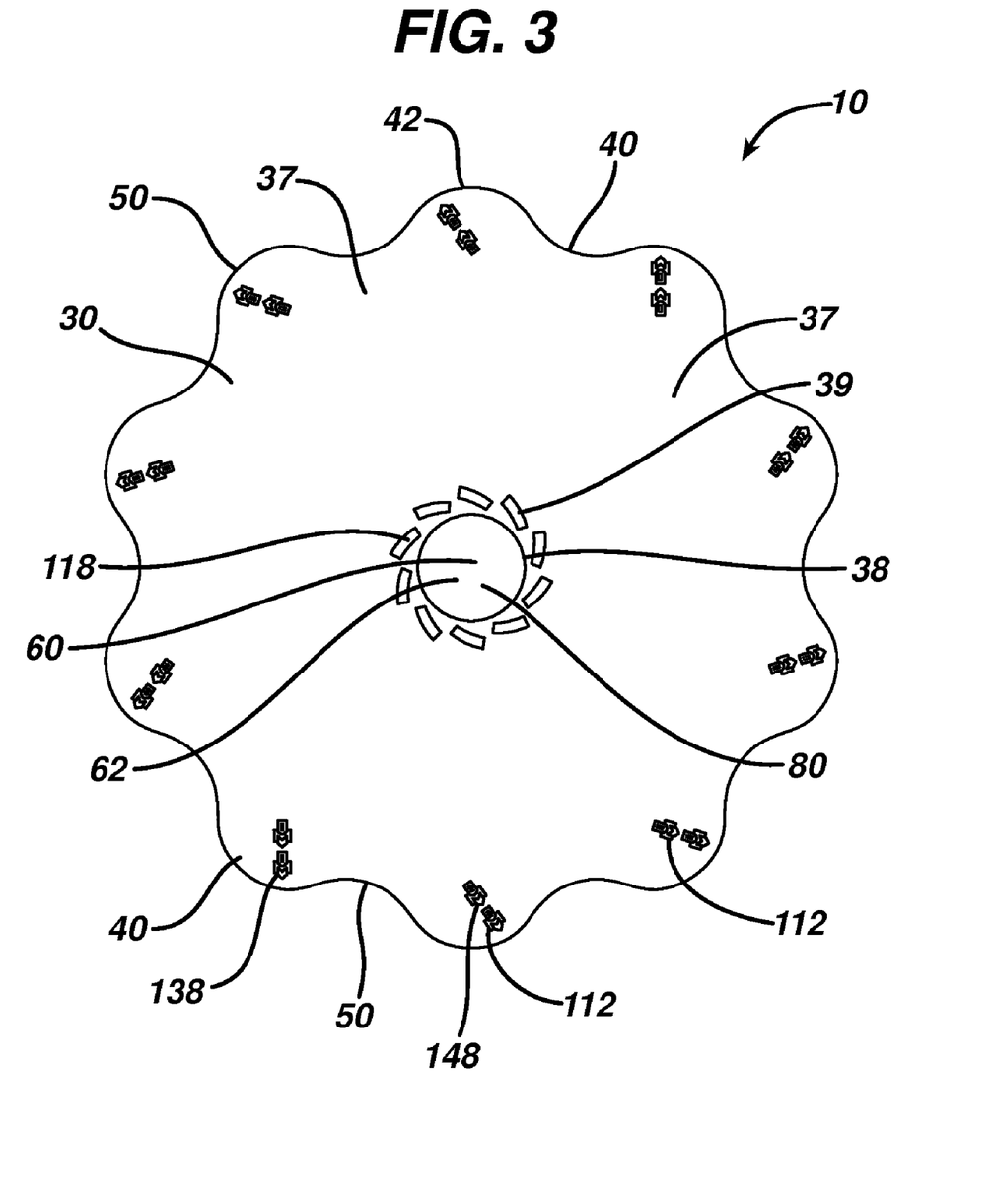
FIG. 3 is a bottom view of the package of FIG. 1
Figure 4:
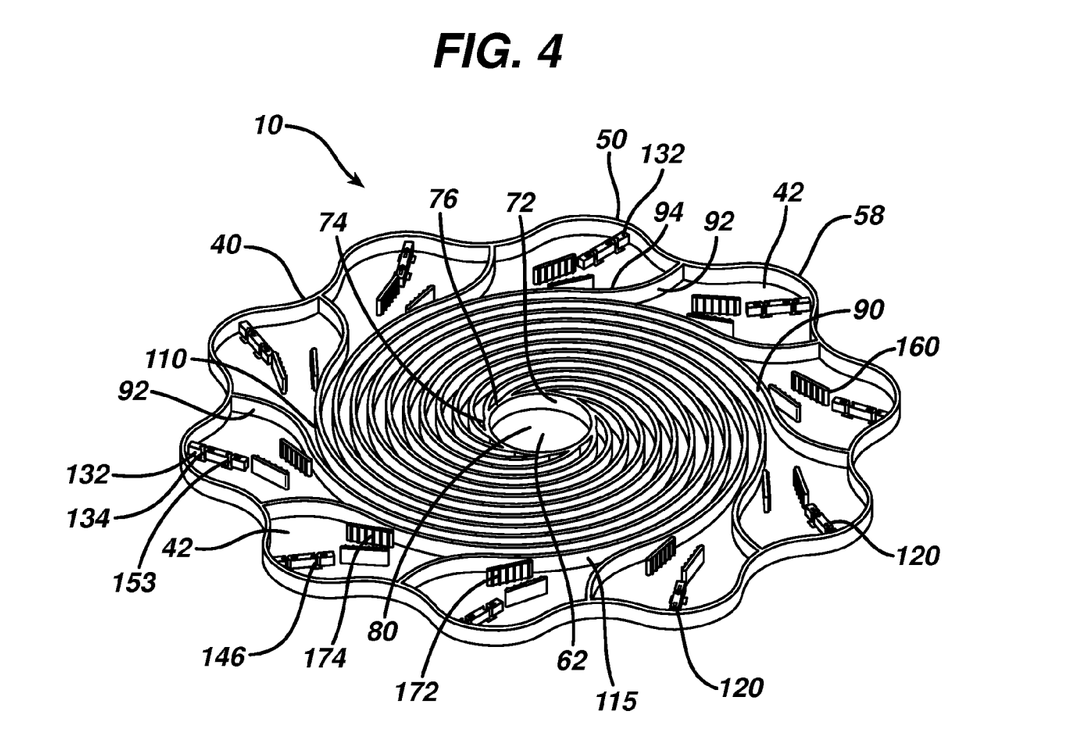
FIG. 4 is a perspective view of the package of FIG. 1.
Figure 5:
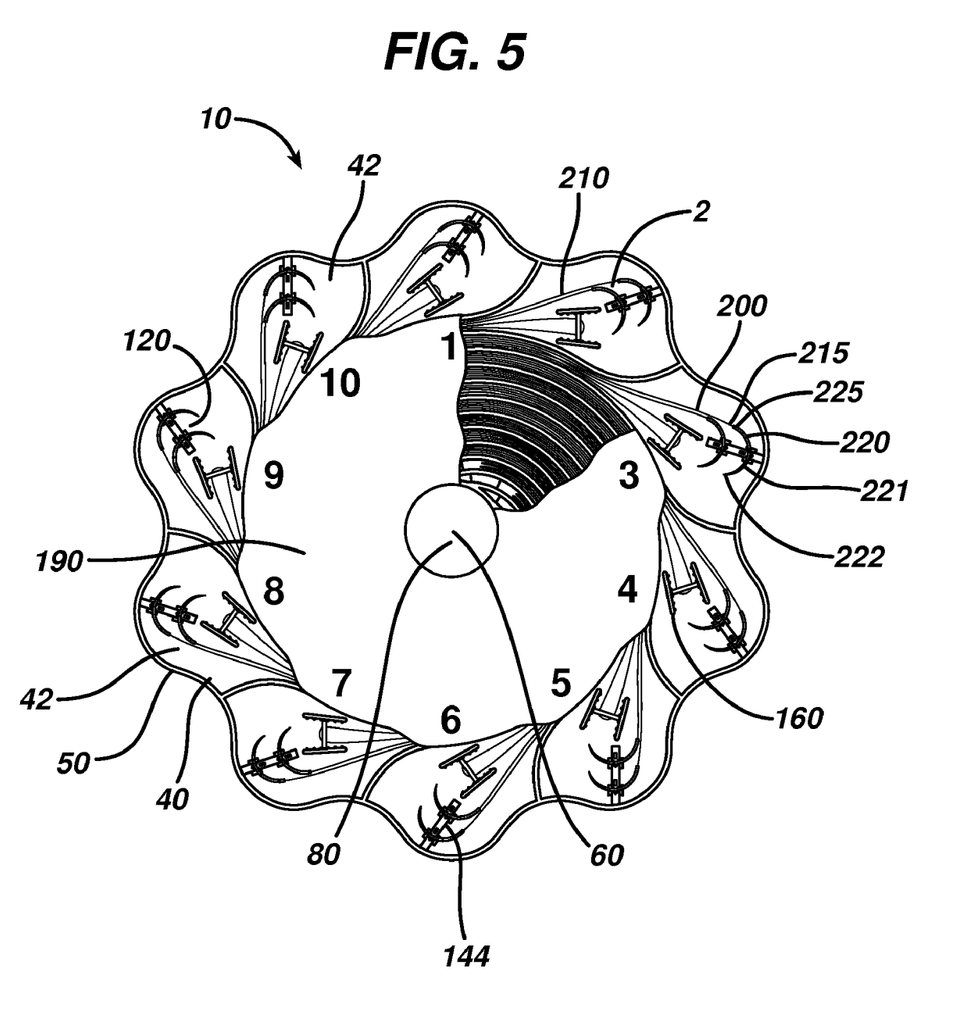
FIG. 5 is a top view of a package of the present invention loaded with double-armed suture, and having a cover mounted to the top; the top is illustrated with a section partially removed to illustrate the tracks and suture in the tracks.

Adjacent to the needle park 120 in platform section 42 is the optional pledget park 160. Pledget park 160 is seen to have a pair of opposed walls 170 having inner surfaces 172 and outer surfaces 174 and tops 176. The walls 170 extend up from surface 34 of floor section 35 and are seen to be angulated with respect to each other, but may also be parallel. Extending inwardly from the inner surfaces 172 are the optional ridge members 174. Spaces 177 are contained between ridge members 174 for receiving a pledget member 230. As seen in FIGS. 5 and 6, an optional cover 190, having top 192, bottom 194 and periphery 196, and optional opening 198, may be mounted to the top of package 10. Preferably the cover 190 is mounted to the walls 90 by affixing the bottom 194 to the tops 94. This maintains sutures loaded into the tracks 110 within the tracks in the event that a loaded package 110 is inverted, as well as during shipping, handling and processing.

Referring now to FIGS. 5 and 6, the double armed suture 200 loaded into the packages 10 of the present invention is seen to have suture strand 210. Strand 210 is seen to have opposed ends 215. Mounted to each end 215 is a surgical needle 220. Surgical needles 220 are seen to have curved, elongated bodies 221 with distal piercing points 222 and proximal suture mounting ends 225. Needles 220 have conventional bore holes (not shown) drilled in their proximal ends 225 to receive the suture ends 215 to which they are mounted by conventional securing methods such as mechanical swaging. Also mounted to the central section 218 of sutures 210 are the conventional pledget members 230. Pledget members 230 are attached or affixed to the central sections 218 of sutures 210 in a conventional manner such as by threading the suture material through slits or holes formed within the pledgets 230. The pledgets 230 may be attached in conventional manners such as by gluing or mechanical fixation. Alternatively, pledgets may be slidably affixed to the suture 210 by for example threading. Pledget members 230 are seen to be substantially rectangular members having thread openings 235 therethrough. The pledget members 230 may have any conventional shape, in addition to the shape shown.

As seen in FIGS. 5 and 6, the package 10 has a plurality of sutures 200 and surgical needles 220 mounted therein. Each suture strand 210 is mounted in an individual track 110, with the suture strands resting upon the bottoms 112 of the tracks 110, and partially upon the top of sections 42. The needles 220 are seen to be mounted in the needle parks 120, with one needle in opening 124 and one needle in opening 126 of each park 120. The pledget member 230 for each suture strand 210 is seen to be mounted in pledget park 160 in spaces 177.

The sutures 200 are loaded into the tray packages 10 in a number of conventional manners. For example, the package 10 may be mounted to a conventional fixture. Then, the needles 220 are mounted in the spaces 124 and 126, respectively, in the parks 120. The optional pledget members 230 are mounted in spaces 177 of pledget park 160. Next, a vacuum may be applied to the openings 38 and 118 drawing or moving a looped section 212 of the suture strand 210 into the track 110. It is preferred that the covers 190 are mounted to the packages 10 prior to vacuum loading the suture strands 210, although optionally a flat fixture may placed over the tops of the tracks in contact with the top surfaces 94 of walls 90 during vacuum loading, and removed after loading for subsequent application of a cover 190. Alternatively, the suture may be placed into the package by a stylus loading technique such as those described in U.S. Pat. No. 5,660,024, U.S. Pat. No. 5,664,404, U.S. Pat. No. 5,491,954, U.S. Pat. No. 5,491,955, US2004/0177594, or US2002/0069617, which are incorporated by reference.

Before or after the armed sutures 200 have been loaded into the trays 10, the optional covers or lids 190 are affixed in a conventional manner. For example, the cover 190 may consist of a heat sealable paper which is mounted to the top surfaces 94 of the spiral walls 90 and heat is applied in a conventional manner via, for example, conductive heat or ultrasound, along with pressure to the heat sealable paper. Alternatively, if cover 190 is made from plastic, it may be welded to the top surface of the spiral tracks. Alternatively, the cover 190 may be mounted via conventional mechanical fixation such as rivets, tabs, etc. Covers 190 are seen to have a central opening 192 and an outer periphery 194 with undulations 196 that correspond to the platform sections 42 adjacent to the corresponding undulations of periphery 40. It is also possible and desirable to optionally label each platform section 42 with a number. This can be accomplished in a variety of ways including molding numbers into the floor 32, and labeling the top 34 of floor 30 in platform sections 42 by printing or applying labels.

It is desirable for each suture 200 to be numbered. This can be accomplished as illustrated in FIG. 6 by printing a number or otherwise labeling a number on the cover 190 adjacent to each platform section After the optional covers 190 are affixed or mounted to the packages 10, the loaded packages 10 are loaded into conventional outer packages such as Tyvek envelopes, foil pouches, thermoformed trays, and the like for sterilization. Conventional sterilization processes may be utilized on the packages 10 of the present invention loaded with sutures 200 including sterilant gas (e.g., ethylene oxide), gamma radiation, plasma and the like. Those skilled in the art will appreciate that it could be possible to use autoclaving, depending upon the material characteristics of the sutures 200 and package 10.

The novel tray suture packages of the present invention have many advantages that include the ability to bring the packages to be brought closer into the surgical site. In addition, the packages of the present invention can be held with one hand by the health care professional while performing other tasks. The package of the present invention permits the health care professional to rotate the package to dial the next suture easily, and this can be accomplished using one hand. The novel packages of the present invention enable health care professionals to easily keep track of the number of sutures being used, and the packages further provide for both 'right-handed' and 'left-handed' needle arming. The packages of the present invention holds pledgets in place without physical deformation within the package, and the novel packages of the present invention further prevent sutures from kinking and provide for smooth tangle free dispensing from the package.

Although this invention has been shown and described with respect to detailed embodiments thereof, it will be understood by those skilled in the art that various changes in form and detail thereof may be made without departing from the spirit and scope of the claimed invention.

We claim:
1. A tray package for surgical sutures, comprising:
a floor member having a top surface, a bottom surface, an outer periphery, a center and a central area about the center;
a central wall extending up from the central area of the floor member, the central wall member having an inner surface, an outer surface and a top;

an outer wall extending up from the periphery of the floor member, the outer wall having an outer surface, and inner surface and a top;

a plurality of platform sections extending radially out from the floor member about the periphery of the floor member; and, a plurality of curvilinear wall members extending up from the top surface of the floor member and extending radially outward from the central area toward the outer periphery of the floor member in a spiral manner forming a plurality of discrete suture tracks, the wall members having opposed outer surfaces, the wall members having proximal ends connected to the outer surface of the central wall, and distal ends connected to the inner surface of the outer wall, the wall members spaced from each other such that each discrete suture track is formed between the outer surfaces of adjacent wall members and the top surface of the floor member, the outer surface of the central wall, and the inner surface of the outer wall, wherein the distal end of each suture track is widened to form a platform section extending radially out about the periphery of the floor member.

2. The tray package of claim 1, additionally comprising a needle park member extending up from the floor member in each platform section.

3. The tray package of claim 1, additionally comprising a pair of spaced apart pledget wall members extending up from the floor member in each platform section, the pledget wall members having inner surfaces, outer surfaces and tops, such that a pledget member may be placed in between the pledget wall members.

4. The tray package of claim 3, wherein the pledget wall members are angulated with respect to each other.

5. The tray package of claim 3, wherein the pledget wall members additionally comprise ridges extending out from the inner surfaces.

6. The tray package of claim 1, additionally comprising a vacuum opening in the floor member in each suture track.

7. The tray package of claim 1, additionally comprising a cover member mounted to the tops of the curvilinear wall members over the tracks, and covering at least a portion of the tracks.

8. The tray package of claim 1, additionally comprising a surgical suture in at least one track.

9. The tray package of claim 2, additionally comprising a needle and surgical suture combination, wherein the needle is mounted in the needle park member and the suture is mounted in a track.

10. The tray package of claim 2 additionally comprising a pair of spaced apart pledget wall members extending up from the floor member in each platform section, the pledget wall members having inner surfaces, outer surfaces and tops, such that a pledget member may be placed in between the pledget wall members.

11. The tray package of claim 10 comprising a surgical needle having a surgical suture and a pledget mounted thereto, wherein the needle is mounted in the needle park member, the pledget is mounted between the pledget wall members, and the suture is contained in a track.

12. The tray package of claim 1 having an opening in the central area of the floor member.

13. The tray package of claim 12, additionally comprising a spindle member mounted in the opening, the spindle member comprising a base plate having a central opening and the opening having a periphery, and a plurality of cantilever members extending upwardly about the periphery of the opening, each cantilever member having a fixed bottom end and a free top end.

14. The tray package of claim 13, wherein the cantilever members comprise flange members extending radially outward from the top end of each cantilever member.

15. The package of claim 1, wherein the floor member is substantially planar.

16. The package of claim 1, wherein the periphery is undulating.

17. The package of claim 1, wherein each track is in communication with an individual platform section.

* * * * *